United States Patent [19]

Su et al.

[11] Patent Number: 4,895,971

[45] Date of Patent: Jan. 23, 1990

[54] PROCESS FOR THE PRODUCTION OF IMINODIACETONITRILE

[75] Inventors: Jow-Lih Su, Silver Spring; Martin B. Sherwin, Potomac, both of Md.

[73] Assignee: W. R. Grace & Co.-Conn., New York, N.Y.

[21] Appl. No.: 264,413

[22] Filed: Oct. 31, 1988

[51] Int. Cl.$^4$ ............................................. C07C 120/00
[52] U.S. Cl. ........................................................ 558/346
[58] Field of Search ........................................ 558/346

[56] References Cited

U.S. PATENT DOCUMENTS

| | | | |
|---|---|---|---|
| 2,608,380 | 10/1946 | Beekhuis | 23/151 |
| 2,794,044 | 5/1957 | Miller | 260/465.5 |
| 3,061,628 | 10/1962 | Singer et al. | 260/465.5 |
| 3,167,580 | 1/1965 | Saunders et al. | 260/465.5 |
| 3,337,607 | 8/1967 | Wollensak | 260/465.5 |
| 3,714,335 | 1/1973 | Kobetz et al. | 423/483 |
| 3,840,581 | 10/1974 | Neumaier et al. | 260/465.5 A |
| 3,856,844 | 12/1974 | Wikman | 260/465.5 A |
| 3,862,203 | 1/1975 | Greco et al. | 260/465.5 A |
| 3,864,378 | 2/1975 | Homberg et al. | 260/465.5 A |
| 3,907,858 | 9/1975 | Davis et al. | 260/465.5 A |
| 3,925,448 | 12/1975 | Lanier | 260/465.5 A |
| 3,950,384 | 4/1976 | Neumaier et al. | 260/465.5 A |
| 3,959,342 | 5/1976 | Homberg et al. | 260/465.5 A |
| 3,984,453 | 10/1976 | Chaberek | 260/465.5 A |
| 3,988,360 | 10/1976 | Gaudette et al. | 558/346 |
| 3,993,681 | 11/1976 | Cullen | 558/346 |
| 4,307,037 | 12/1981 | Suchsland et al. | 260/465.5 A |
| 4,478,759 | 10/1984 | Distler et al. | 558/346 |
| 4,485,049 | 11/1984 | Lannert et al. | 260/465.5 R |
| 4,543,215 | 9/1985 | Brunnmueller et al. | 260/465.5 R |
| 4,661,614 | 4/1987 | Most et al. | 558/346 |
| 4,731,465 | 3/1988 | Shen et al. | 558/346 |
| 4,745,207 | 5/1988 | Brunnmueller et al. | 558/351 |

FOREIGN PATENT DOCUMENTS 0102343 3/1984 European Pat. Off. .
0102935 3/1984 European Pat. Off. .

OTHER PUBLICATIONS

Kirk-Othmer Encyclopedia of Chemical Technology, 2nd Ed., vol. 6, "Cyanides (Hydrogen Cyanides)", pp. 582–583 (1965).

*Primary Examiner*—Joseph Paul Brust
*Attorney, Agent, or Firm*—James P. Barr

[57] ABSTRACT

This invention relates to the production of iminodiacetonitrile, and more specifically to an integrated process wherein a crude, unpurified reactor gas stream from a hydrogen cyanide reactor and optionally, a crude, unpurified reactor gas stream from a formaldehyde process reactor are fed directly to a reactive absorber together with additional ammonia and acidified water to produce iminodiacetonitrile in high yields. This process provides improved economics for producing iminodiacetonitrile by eliminating costly intermediate recovery and purification processes associated with conventional hydrogen cyanide and formaldehyde production processes.

28 Claims, 3 Drawing Sheets

PROCESS FOR THE PRODUCTION OF IMINODIACETONITRILE

BACKGROUND OF THE INVENTION

Field of the Invention

This invention relates to the production of iminodiacetonitrile, and more specifically to an integrated process wherein a crude, unpurified reactor gas stream from a hydrogen cyanide reactor and optionally, a crude, unpurified reactor gas stream from a formaldehyde process reactor are fed directly to a reactive absorber together with additional ammonia and acidified water to produce iminodiacetonitrile in high yields. This process provides improved economics for producing iminodiacetonitrile by eliminating costly intermediate recovery and purification processes associated with conventional hydrogen cyanide and formaldehyde production processes.

It is known in the prior art that iminodiacetonitrile can be prepared by reacting formaldehyde, hydrogen cyanide and ammonia in aqueous solutions. While the order of the reactant addition may vary in practice, the overall reaction can be written as follows:

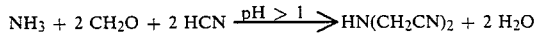

On an industrial scale, the conventional process for the production of iminodiacetonitrile is reliant upon commercially available, purified hydrogen cyanide and formaldehyde reactants.

Commercially available hydrogen cyanide is produced primarily by the ammoxidation of methane (Andrussow Process or the Degussa process, also called the BMA process), the reaction of ammonia and propane (Fluohmic process), the ammoxidation of methanol, the decomposition of formamide, and the recovery of hydrogen cyanide as the by-product in the preparation of acrylonitrile by the ammoxidation of propylene (SOHIO process). These and other similar processes are well documented in the art. Since all of these processes either use ammonia as the source of nitrogen or have ammonia present as a by-product, the hydrogen cyanide reactor product gas streams contain some unreacted ammonia. This unreacted ammonia must be removed before recovering hydrogen cyanide to avoid dangerous exothermic polymerization of the liquid hydrogen cyanide. Therefore each of these processes must employ a general three-stage process wherein:

(1) a crude, dilute gaseous hydrogen cyanide product stream is formed by one of the above listed methods, product
(2) excess unreacted ammonia in the reactor product gas stream is removed, and recovered by selective absorption and stripping, and
(3) purified hydrogen cyanide is obtained by water scrubbing followed by stripping out the water solvent. (See FIG. 1)

Each of these three stages in the manufacturing process has substantial capital requirements, which in turn requires a substantially large scale operation for any of these processes to be economically feasible.

The predominant processes for the production of commercial grade formaldehyde are by the dehydrogenation of methanol over silver catalyst (BASF process) or by the oxidation of methanol over a metal oxide catalyst such as ferric molybdate.

The reaction using the silver catalyst is endothermic, and may be written as follows:

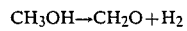

The reaction using ferric molybdate catalyst is exothermic, and may be written as follows:

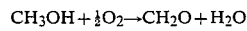

Both of the above commercial processes employ a general two-stage process wherein:

(1) A crude, dilute formaldehyde product stream is produced, and
(2) formaldehyde is recovered by aqueous absorption columns.

Substantial capital equipment costs can be attributed to the large absorption columns required to obtain commercial grade formaldehyde, which therefore requires a large scale production plant to afford economically feasibility.

Under the process of this invention, much of these recovery and purification equipment costs can be eliminated. That is, in the production of hydrogen cyanide, the crude reactor product stream is a mixture containing, in addition to hydrogen cyanide, a significant amount of ammonia and excess water. Similarly, in the production of formaldehyde, the crude reactor product stream contains, in addition to formaldehyde, a significant amount of excess water. Under the process of this invention, it has been discovered that it is not necessary, and in fact, is actually redundant to first remove this unreacted ammonia and/or excess water from the crude reactor gas product streams, only to reintroduce it in the down-stream reactor when forming iminodiacetonitrile. This is because it has now been found that it is possible to combine these crude reactor product streams directly to achieve high yields of iminodiacetonitrile product. The high yields obtained by this invention were unexpected and not obvious since similar attempts to produce other acetonitrile products such as nitrilotriacetonitrile or ethylenediamintetraacetonitrile using this same process were unsuccessful. For example, crude reactor streams containing formaldehyde and hydrogen cyanide were produced and fed directly into a reactive absorber together with an additional ammonia source. When scrubbed with a solution of pH 0–1, a range that favored the production of nitrilotriacetonitrile, a yield of less than 40% was obtained. A similar process, utilized the addition of ethylenediamine in the place of ammonia, and a scrubbing solution of pH=0.8 which favored the production of ethylendiaminetetracetonitrile, produced yields of approximately 25%. In comparison, this process as described in the detailed description, when applied to the production of iminodiacetonitrile, produced yields in excess of 80%.

OBJECTS OF THE INVENTION

An object of this invention is to provide a new and improved process for the production of iminodiacetonitrile.

A further object of this invention is to provide a simple integrated process for the production of iminodiacetonitrile.

A further object of this invention is to provide an improved process for the production of iminodiacetonitrile wherein conventional reactant purification and recovery processes are eliminated, yet product is obtained in high yield.

These and other objects will be apparent from the remaining specification and the appended claims.

DETAILED DESCRIPTION

The subject process is directed to a means of producing iminodiacetonitrile in high yields by directly integrating the crude, unpurified reactor gas streams from the production processes of hydrogen cyanide and formaldehyde into a simple one-step iminodiacetonitrile formation process, thereby eliminating conventional formaldehyde recovery and hydrogen cyanide purification and recovery processes.

Specifically, under the process of this invention two reactor gas streams, one containing unpurified, crude hydrogen cyanide, the other containing unpurified, crude formaldehyde, together with an additional ammonia source, are reacted in a reactive absorber and scrubbed with a suitable aqueous reactive scrubbing solution. Suitable types of reactive absorbers can be bubble column, packed column, tray column, or the like, and is preferably a bubble column. Those processes capable of forming crude reactant gas streams suitable for use in this invention are those hydrogen cyanide and formaldehyde processes previously discussed in the background of this invention. Contemplated equivalents are those processes that are simple variations of the given examples but produce gas streams having concentrations of hydrogen cyanide or formaldehyde substantially similar to the acceptable ranges disclosed in this invention. The relative proportions of each of the reactants is substantially stoichiometric, but each may vary by as much as 50 percent.

The aqueous scrubbing solution is recycled continuously to the reactive absorber. That is, a portion of the mother liquor containing the formed iminodiacetonitrile is first withdrawn from the bottom of the reactive absorber, the iminodiacetonitrile is then separated by cooling and evaporative crystallization, and finally the mother liquor is recycled back into the reactive absorber.

Figure 1:
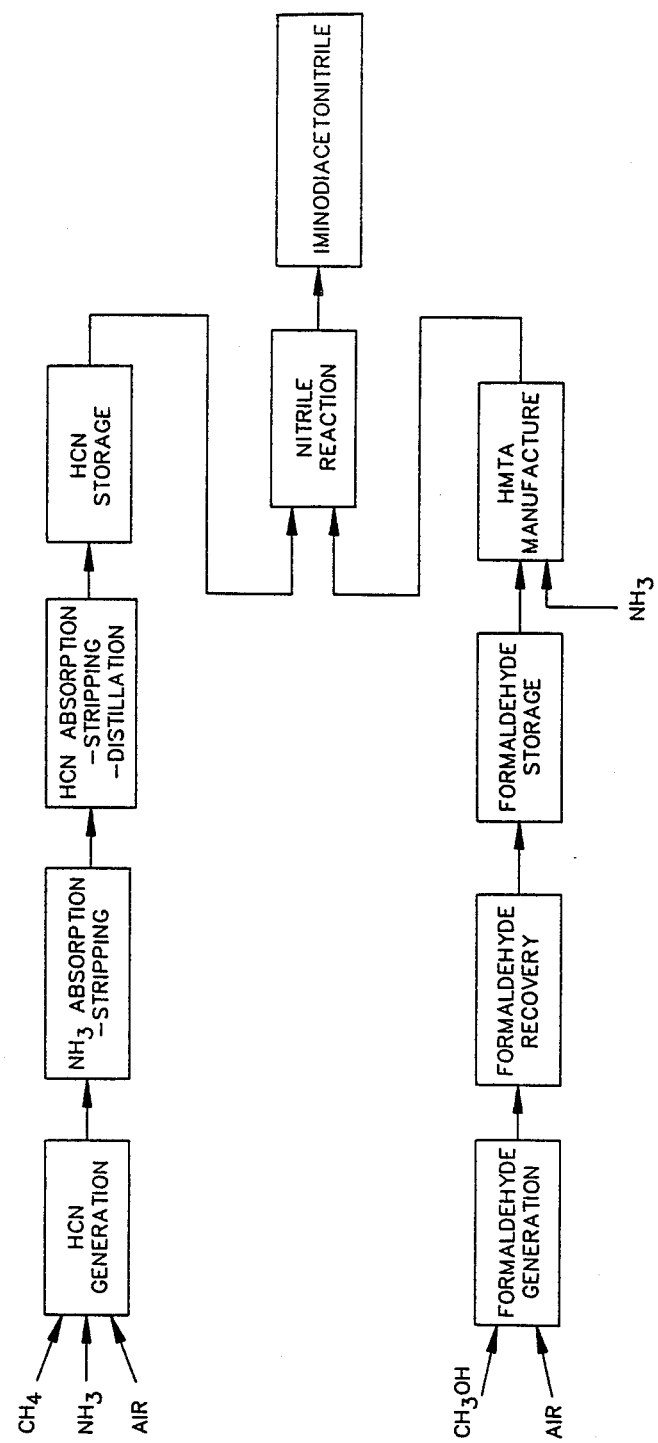
Figure 2:
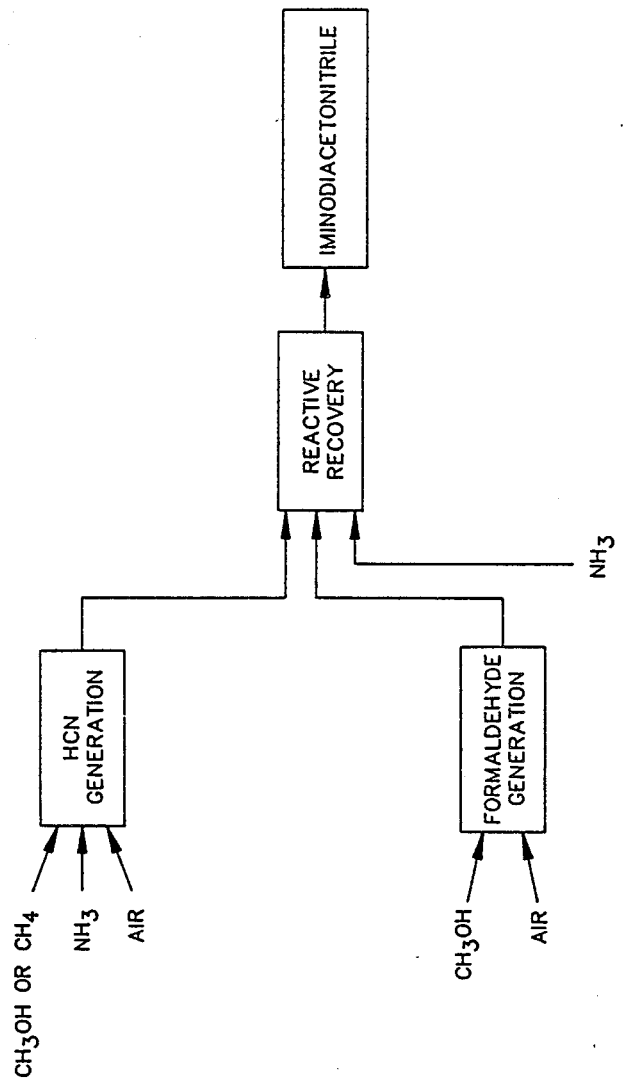

A first embodiment of this invention is directed to the process where hydrogen cyanide and formaldehyde are produced in respective upstream reactors and their product gas streams are fed into a reactive absorber together with an additional gaseous or liquid ammonia stream and acidified water (FIG. 2). In this embodiment, the reactive absorber is maintained at a temperature between 25° and 90° C., and preferably between 50° and 70° C. The pressure maintained within the reactive absorber is maximized to enhance absorption, and it is typically 5 to 10 psig, as practiced in this invention. The residence time of the liquid reactants in the reactive absorber can be varied between 0.5 and 10 hours, and is preferably 2 to 5 hours. The aqueous scrubbing solution is a dilute acid solution, and may also contain hexamethylenetetramine, ammonium sulfate, or other amines as well as recycled iminodiacetonitrile, iminodiacetonitrile mother liquor, and other product intermediates. Any mineral acid can be used in the scrubbing solution to maintain the pH in the proper range and is typically sulfuric acid. The aqueous scrubbing solution is maintained at a pH between 2 and 10, and preferably between pH 6 and 8.

Figure 3:
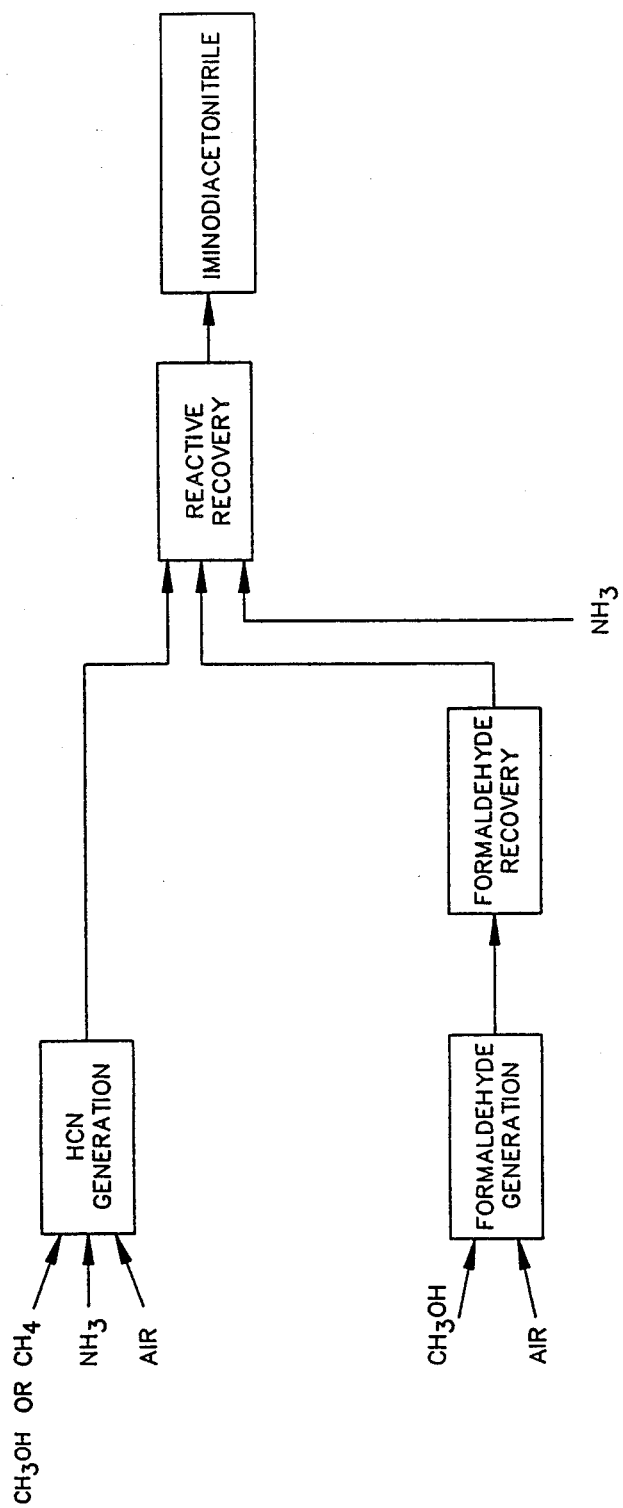

A second embodiment of this invention is directed to the process where a crude, dilute formaldehyde reactor product stream is produced and fed into an aqueous absorption column where formaldehyde is recovered as an aqueous solution (FIG. 3). In a separate reactor, a crude dilute hydrogen cyanide reactor product stream is produced, which, together with the recovered aqueous formaldehyde solution, is fed directly into a reactive absorber along with an additional gaseous or liquid ammonia stream and acidified water. The reactive absorber is maintained at a temperature between 25° and 90° C., and preferably between 50° and 70° C. The pressure maintained on the reactive absorber is maximized to enhance absorption, and it is typically 5 to 10 psig, as practiced in this invention. The residence time of the liquid reactants in the reactive absorber can be varied between 0.5 and 10 hours, and is preferably 2 to 5 hours. The aqueous scrubbing solution is a dilute acid solution, or in this embodiment may also be the recovered aqueous formaldehyde solution. In addition, the aqueous scrubbing solution may also contain hexamethylenetetramine, ammonium sulfate, or other amines as well as recycled iminodiacetonitrile, iminodiacetonitrile mother liquor and other product intermediates. Any mineral acid can be used in the scrubbing solution to maintain the pH in the proper range and is typically sulfuric acid. The aqueous scrubbing solution is maintained at a pH between 2 and 10, and preferably between pH 6 and 8.

A preferred process for producing a crude hydrogen cyanide reactor gas stream for use in the invention is the ammoxidation of methanol. In this process, methanol is vaporized and mixed with ammonia, nitrogen and oxygen and passed through a reactor packed with a ferric molybdate catalyst at elevated temperatures. The typical temperatures are in the range 300°–500° C. and typical pressures are 2–20 psig. It is desirable that the concentration of hydrogen cyanide in the reactant gas stream be maximized for easiest product recovery. The typical hydrogen cyanide concentration of the crude reactor product gas stream is in the range 5–10 mole percent.

One of the preferred processes for producing the crude formaldehyde reactor gas stream in this invention is the catalytic oxidation of methanol over a ferric molybdate catalyst. The typical concentration of formaldehyde in the crude reactor product gas stream is 5–10 mole percent and, as in the case of hydrogen cyanide, is preferably as high as possible for easiest product recovery.

Without further elaboration, it is believed that one skilled in the art, using the preceding description, can utilize the present invention to its fullest extent. The following examples are provided to illustrate the invention in accordance with the principles of this invention, but are not to be construed as limiting the invention in any way except as indicated in the appended claims. All parts and percentages are by moles unless otherwise indicated.

EXAMPLE 1

Hydrogen cyanide and formaldehyde were produced in respective upstream reactors, cooled and fed directly into a reactive absorber together with an additional ammonia stream and $H_2SO_4$ acidified water. The reactive absorber solution was recycled with continuous addition of $H_2SO_4$ to maintain a constant pH range of 6.0 to 8.0. The reactive absorber was maintained at 65°–70° C., with a presence of 10 psig.

| Reactive Absorber Starting Solution: | 1500 g. H₂O (pH 6.5) |
|---|---|
| Gaseous Feed Composition: | HCN: 0.321 moles/hr. |
| | CH₂O: 0.330 moles/hr. |
| | NH₃: 0.457 moles/hr. |
| | O₂: 1.547 moles/hr. |
| | N₂: 19.260 moles/hr. |
| | CO: 0.287 moles/hr. |
| | H₂O: 0.900 moles/hr. |
| Temperature: | 65–70° C. |
| Pressure: | 10 psig. |
| pH - | maintained at 6–8 by continuous addition of H₂SO₄. |

| Reaction time (Hr.) | Total IDAN formed (moles) In Solution | Total IDAN formed (moles) As Precipitate | IDAN Yield percent based on the absorbed: HCN | IDAN Yield percent based on the absorbed: CH₂O |
|---|---|---|---|---|
| 1 | 0 | 0 | 0 | 0 |
| 2 | 0.019 | 0 | 6.0 | 5.8 |
| 3 | 0.084 | 0 | 17.4 | 16.9 |
| 4 | 0.155 | 0 | 24.2 | 23.5 |
| 5 | 0.630 | 0 | 74.7 | 72.6 |
| 8 | 0.822 | 0.211 | 80.4 | 78.1 |
| 10 | 0.787 | 0.558 | 83.8 | 81.4 |

EXAMPLE 2

The experiment as described in Example 1 was repeated except that the temperature of the reactive absorber was maintained at 60° C.

| Reactive Absorber Starting Solution: | 1500 g. H₂O (pH 6.5) |
|---|---|
| Gaseous Feed Composition: | HCN: 0.47 moles/hr. |
| | CH₂O: 0.50 moles/hr. |
| | NH₃ 0.30 moles/hr. |
| | O₂ 1.34 moles/hr. |
| | N₂ 19.76 moles/hr. |
| | CO 0.27 moles/hr. |
| | H₂O 2.44 moles/hr. |
| Temperature: | 60° C. |
| Pressure: | 10 psig. |
| pH | maintained at 6–8 by continuous addition of H₂SO₄. |

HCN absorption efficiency in the reactive absorber varied from 83–95%.

| Reaction Time (Hr.) | IDAN Formed (Moles) | IDAN Yield Percent (based on absorbed hydrogen cyanide) |
|---|---|---|
| 0–5.5 | 0.96[a] | 86% |
| 5.5–11.5 | 0.95[b] | 79% |
| 11.5–16.5 | 0.72[b] | 62% |
| 16.5–21.5 | 0.85[b] | 85% |

[a]dissolved in scrubbing solution
[b]recovered as precipitate

EXAMPLE 3

The experiment as described in Example 2 is repeated except that the source of formaldehyde is in the form of a 50% aqueous solution recovered from an absorption column. This solution, together with an additional ammonia source is used to scrub the hydrogen cyanide reactor gas stream in a reactive absorber. Similar yields of iminodiacetonitrile are realized.

From the foregoing examples, and description of the preferred embodiments, one skilled in the art can easily ascertain the essential characteristics of this invention, and without departing from the spirit and the scope thereof, can make various changes and modifications of the invention to adapt it to various usages and conditions.

What is claimed is:

1. An improved process for the production of iminodiacetonitrile prepared by
    (a) contacting under reaction conditions in a reactive absorber
        (1) hydrogen cyanide
        (2) formaldehyde
        (3) ammonia
    (b) scrubbing the reaction products from (a) supra with an aqueous scrubbing solution,
    (c) recovering the product,
wherein the improvement comprises: using as a source of hydrogen cyanide in step
    (a) the direct unpurified reactor product gases of a hydrogen cyanide production process comprising a gaseous mixture of hydrogen cyanide and ammonia,
using as a source of formaldehyde in step (a) the direct unpurified reactor product gases of a formaldehyde production process comprising a gaseous mixture of formaldehyde and water.

2. The improved process for the production of iminodiacetonitrile in claim 1 wherein the hydrogen cyanide, formaldehyde and ammonia are contacted in substantially stoichiometric amounts.

3. The improved process for the production of iminodiacetonitrile in claim 1 wherein the reactive absorber is maintained at a pressure in the range 0 to 200 psig.

4. The improved process for the production of iminodiacetonitrile in claim 1 wherein the reactive absorber is maintained at a pressure in the range 5 to 10 psig.

5. The improved process for the production of iminodiacetonitrile in claim 1 wherein the aqueous reactive absorber solution is maintained in the range pH 1 to pH 10 by the continuous addition of acid.

6. The improved process for the production of iminodiacetonitrile in claim 1 wherein the aqueous reactive absorber solution is maintained in the range pH 6 to pH 8 by the continuous addition of acid.

7. The improved process for the production of iminodiacetonitrile in claim 1 wherein the aqueous reactive absorber solution is maintained at a temperature ambient to 150° C.

8. The improved process for the production of iminodiacetonitrile in claim 1 wherein the reactive absorber is maintained at a temperature in the range 65° to 70° C.

9. The improved process for the production of iminodiacetonitrile in claim 1 wherein hexamethylenetetramine is used in the reactive absorber solution.

10. The improved process for the production of iminodiacetonitrile in claim 1 wherein ammonium sulfate is used in the reactive absorber solution.

11. The improved process for the production of iminodiacetonitrile in claim 1 wherein the crude, unpurified formaldehyde reactor product gas is produced by a process wherein methanol is oxidized over a ferric molybdate catalyst.

12. The improved process for the production of iminodiacetonitrile in claim 1 wherein the crude, unpurified formaldehyde reactor product gas is produced by the process wherein methanol is dehydrogenated over a silver catalyst.

13. The improved process for the production of iminodiacetonitrile in claim 1, wherein the process for producing the crude, unpurified hydrogen cyanide reactor product gas is selected from the group consisting of the ammoxidation of methane, the ammoxidation of methanol, the reaction of ammonia and propane, the decomposition of formamide, and the recovery of hydrogen cyanide from the ammoxidation of propylene.

14. The improved process for the production of iminodiacetonitrile in claim 1 wherein the crude, unpurified hydrogen cyanide reactor product gas is produced by methanol ammoxidation process.

15. An improved process for the production of iminodiacetonitrile prepared by
   (a) contacting under reaction conditions in a reactive absorber
      (1) hydrogen cyanide
      (2) formaldehyde
      (3) ammonia
   (b) scrubbing the reaction products from (a) supra with an aqueous scrubbing solution, and
   (c) recovering the product,
wherein the improvement comprises:
   using as a source of hydrogen cyanide in step (a) the direct unpurified reactor product gas of the ammoxidation of methanol comprising a gaseous mixture of hydrogen cyanide and ammonia,
   using as a source of formaldehyde in step (a) the direct unpurified reactor product gas of the oxidation of methanol over a ferric molybdate catalyst comprising a gaseous mixture of formaldehyde and water,
   maintaining the reactor at a pressure in the range 5 to 10 psig, at a temperature in the range 65° to 70° C., and
   using an aqueous reactive absorber solution having a pH in the range 6 to 8.

16. An improved process for the production of iminodiacetonitrile prepared by
   (a) contacting under reaction conditions in a reactive absorber
      (1) hydrogen cyanide
      (2) formaldehyde
      (3) ammonia
   (b) scrubbing the reaction products from (a) supra with an aqueous scrubbing solution, and
   (c) recovering the product,
wherein the improvement comprises:
   using as a source of hydrogen cyanide in step (a) the direct, unpurified reactor product gases of a hydrogen cyanide production process comprising a gaseous mixture of hydrogen cyanide and ammonia,
   using as a source of formaldehyde in step (a) the aqueous formaldehyde solution obtained from an absorption column of a formaldehyde production process.

17. The improved process for the production of iminodiacetonitrile in claim 16 wherein the reactive absorber is maintained at a presence in the range 0 to 200 psig.

18. The improved process for the production of iminodiacetonitrile in claim 16 wherein the reactive absorber is maintained at a pressure in the range 5 to 10 psig.

19. The improved process for the production of iminodiacetonitrile in claim 16 wherein the aqueous reactive absorber solution is maintained in the range pH 1 to pH 10 by the continuous addition of acid.

20. The improved process for the production of iminodiacetonitrile in claim 16 wherein the aqueous reactive absorber solution is maintained in the range pH 6 to pH 8 by the continuous addition of acid.

21. The improved process for the production of iminodiacetonitrile in claim 16 wherein the aqueous reactive absorber solution is maintained at a temperature ambient to 150° C.

22. The improved process for the production of iminodiacetonitrile in claim 16 wherein the reactive absorber is maintained at a temperature in the range 65° to 70° C.

23. The improved process for the production of iminodiacetonitrile in claim 16 wherein hexamethylenetetramine is used in the reactive absorber solution.

24. The improved process for the production of iminodiacetonitrile in claim 16 wherein ammonium sulfate is used in the reactive absorber solution.

25. The improved process for the production of iminodiacetonitrile in claim 16 wherein the crude, unpurified formaldehyde reactor product gas is produced by a process wherein methanol is oxidized over a ferric molybdate catalyst.

26. The improved process for the production of iminodiacetonitrile in claim 16 wherein the crude, unpurified formaldehyde reactor product gas is produced by the process wherein methanol is dehydrogenated over a silver catalyst.

27. The improved process for the production of iminodiacetonitrile in claim 16, wherein the process for producing the crude, unpurified hydrogen cyanide reactor product gas is selected from the group consisting of the ammoxidation of methane, the ammoxidation of methanol, the reaction of ammonia and propane, the decomposition of formamide, and the recovery of hydrogen cyanide from the ammoxidation of propylene.

28. The improved process for the production of iminodiacetonitrile in claim 16 wherein the crude, unpurified hydrogen cyanide reactor product gas is produced by methanol ammoxidation process.

* * * * *